United States Patent [19]

Withington

[11] 4,140,760

[45] Feb. 20, 1979

[54] PHARMACEUTICAL COMPOSITIONS FOR USE IN THE SUPPRESSION OF GASTRIC REFLUX

[75] Inventor: Roger Withington, Shefford, England

[73] Assignee: Reckitt & Colman Products Limited, London, England

[21] Appl. No.: 783,957

[22] Filed: Apr. 1, 1977

[30] Foreign Application Priority Data

Nov. 9, 1976 [GB] United Kingdom ............... 46543/76

[51] Int. Cl.$^2$ ...................... A61K 31/78; A61K 31/70; A61K 31/10; A61K 33/00
[52] U.S. Cl. ...................................... 424/81; 424/127; 424/156; 424/180
[58] Field of Search ................... 424/156, 127, 81, 180

[56] References Cited

U.S. PATENT DOCUMENTS

| | | | |
|---|---|---|---|
| 3,326,755 | 6/1967 | Sheth | 424/156 |
| 3,330,729 | 7/1967 | Johnson, Jr. | 424/81 |
| 3,767,794 | 10/1973 | McVean et al. | 424/127 |

OTHER PUBLICATIONS

Handbook of Non-Prescription Drugs (1) – Amer. Pharm. Assoc., Wash., D.C., (1967), pp. 9 & 12.

Handbook of Non-Prescription Drugs, Fifth Ed., Amer. Pharm. Assoc., Wash., D.C., pp. 7, 9, 10, 11 & 12.
The Extra Pharmacopdeia, The Pharm. Press, London, pp. 127 & 2050.

*Primary Examiner*—Frederick E. Waddell
*Attorney, Agent, or Firm*—Bacon & Thomas

[57] ABSTRACT

A pharmaceutical composition for the suppression of gastric reflux comprises a low viscosity grade sodium alginate, from 0.16 to 2.60 parts by weight of sodium bicarbonate per part by weight of sodium alginate and from 0.10 to 1.04 parts by weight of calcium carbonate per part by weight of sodium alginate. These compositions may be presented in the form of dry powders which can be admixed with water to provide a palatable liquid preparation. However, preferably the compositions are presented in liquid form and a particularly preferred liquid composition comprises an aqueous medium containing 4.0 to 6.0% weight/volume of a low viscosity grade sodium alginate, 2.0 to 3.5% weight/volume of sodium bicarbonate, 1.2 to 2.0% weight/volume of calcium carbonate and 0.6 to 1.2% weight/volume of the sodium salt of an acrylic polymer crosslinked with 1% allyl-sucrose.

14 Claims, No Drawings

PHARMACEUTICAL COMPOSITIONS FOR USE IN THE SUPPRESSION OF GASTRIC REFLUX

FIELD OF THE INVENTION

The present invention relates to pharmaceutical compositions. In particular, the invention relates to preparations for use in the suppression of gastric reflux and, more particularly, albeit not exclusively to such compositions in liquid form.

BACKGROUND OF THE INVENTION AND PRIOR ART

Hitherto, treatments for the suppression of gastric reflux have included the use of solid preparations containing alginic acid, antacid material and sodium bicarbonate. An example of such a preparation, available in tablet or granule form, contains per dosage (two tablets or a single sachet of granules) as active ingredients 0.52 g alginic acid, 0.52 g sodium alginate, 0.26 g of a mixture of magnesium trisilicate and aluminium hydroxide gel, and 0.2 g sodium bicarbonate, in an inert base. The preparation has to be well chewed and, on chewing, the alginic acid reacts with the sodium bicarbonate in the presence of saliva in the buccal cavity to produce carbon dioxide and a highly viscous solution of sodium alginate, the density of which is reduced by entrapped carbon dioxide. The result of this reaction is a mixture not acceptably palatable to everybody it being in the form of a foaming, viscous, sticky mass which has an unpleasant mouthfeel and tends to adhere to the teeth. When the sticky mass is swallowed it then reacts further with gastric acid to form a carbonated raft of alginic acid which floats on the contents of the stomach and thereby suppresses gastric reflux. In the case of infants, such a preparation for the suppression of gastric reflux has been presented in the form of a powder for mixing with water which again results in a sticky foaming mass that can be swallowed by the infant often only with difficulty.

We have now developed a preparation for the suppression of gastric reflux containing sodium alginate which preparation is palatable and reacts with gastric acid to form a raft on the contents of the stomach.

SUMMARY OF THE INVENTION

According to the present invention there is provided a pharmaceutical composition for the suppression of gastric reflux which comprises a low viscosity grade sodium alginate for which the viscosity of a 1% aqueous solution, when determined on a Brookfield viscometer model RVT using spindle No 1 at 20 r.p.m. at 25° C. is within the range of from 3 to 60 centipoise, from 0.16 to 2.60 parts by weight of sodium bicarbonate per part by weight of sodium alginate and from 0.10 to 1.04 parts by weight of calcium carbonate per part by weight of sodium alginate.

DESCRIPTION OF THE PREFERRED EMBODIMENTS

Alginic acid and its salts such as sodium alginate, which are extracted from brown algae, are composed of 1,4′-linked residues of $\beta$-D-mannuronic acid and $\alpha$-L-guluronic acid in varying proportions according to the source of the brown algae and the method of extraction. One of the most useful properties of the water-soluble alginates is their ability to form viscous solutions at low concentrations. Because of the varied composition of the alginates different alginates at the same concentration give solutions of differing viscosity. By the term "low viscosity grade sodium alginate" as used herein is meant those grades of sodium alginate for which the viscosity of a 1% aqueous solution, when determined on a Brookfield viscometer model RVT using spindle No 1 at 20 r.p.m. at 25° C., falls within the range of from 3 to 60 centipoises. Examples of suitable commercial grades include Protanal LF 5/60 which has a viscosity of 10 centipoise, Protanal LF 250 which has a viscosity of 60 centipoise, Protanal LF 5/120 M which has a viscosity of 20 centipoise (Protan + Fagertun, Norway), Manucol LHF which has a viscosity of 40 centipoise and Manucol LB which has a viscosity of 3 centipoise (Alginate Industries Limited, Great Britain).

It will be understood that the sodium alginate for use in the present invention may contain a minor proportion of calcium alginate, for example about 10% by weight of calcium alginate. Certain sodium alginates containing calcium alginate are indeed commercially available.

The pharmaceutical compositions of the present invention preferably comprise a low viscosity grade sodium alginate for which the viscosity of a 1% aqueous solution, when determined on a Brookfield viscometer model RVT using spindle No 1 at 20 r.p.m. at 25° C. is within the range of from 3 to 60 centipoise, from 0.33 to 0.88 parts by weight of sodium bicarbonate per part by weight of sodium alginate and from 0.2 to 0.5 parts by weight of calcium carbonate per part by weight of sodium alginate.

The pharmaceutical compositions of the present invention may be presented in the form of dry powders which can be admixed with water. It will readily be appreciated that the amount of water with which the dry powder is admixed should be so chosen so that a palatable liquid preparation is obtained. However, in a preferred embodiment of the present invention the compositions are presented in liquid form.

The present invention thus includes within its scope a pharmaceutical composition in liquid form for the suppression of gastric reflux which comprises an aqueous medium containing 2.5 to 8.0% weight/volume of a low viscosity grade sodium alginate for which the viscosity of a 1% aqueous solution, when determined on a Brookfield viscometer model RVT using spindle No 1 at 20 r.p.m. at 25° C. is within the range of from 3 to 60 centipoise, 1.3 to 6.5% weight/volume of sodium bicarbonate and 0.8 to 2.6% weight/volume of calcium carbonate.

In the pharmaceutical preparations in liquid form the low viscosity grade sodium alginate is preferably contained in an amount of from 4.0 to 6.0% weight/volume. Preferably, the low viscosity grade sodium alginate employed has a viscosity, when determined in the above-described manner, in the range of from 3 to 40 centipoise, most preferably in the range of from 3 to 20 centipoise.

It will be understood by those skilled in the art that, when the low viscosity grade sodium alginate employed in formulating the compositions of the invention has a viscosity towards the top end of the range stated above, then there may be a practical limit to the amount of the sodium alginate which can be incorporated into the compositions to give pourable liquid preparations.

The liquid compositions of the invention generally also contain a suspending agent in an amount effective to maintain the calcium carbonate in suspension. The choice of suspending agent will depend upon various factors including the amount and grade of sodium alginate used in the compositions and the amount, density and particle size of the calcium carbonate to be maintained in suspension. Preferably, the liquid compositions contain from 0.3 to 1.7% weight/volume of a suspending agent selected from the sodium salt of an acrylic polymer cross-linked with less than 3% allyl-sucrose, tragacanth, pectin, pregelatinised potato starch and sodium starch glycolate, or mixtures of two or more thereof.

In a particularly preferred aspect of the present invention the pharmaceutical composition in liquid form comprises an aqueous medium containing 4.0 to 6.0% weight/volume of a low viscosity grade sodium alginate for which the viscosity of a 1% aqueous solution, when determined on a Brookfield viscometer model RVT using spindle No 1 at 20 r.p.m. at 25° C. is within the range of from 3 to 60 centipoise, 2.0 to 3.5% weight/volume of sodium bicarbonate, 1.2 to 2.0% weight/volume of calcium carbonate and 0.6 to 1.2% weight/volume of the sodium salt of an acrylic polymer cross-linked with 1% allyl-sucrose.

In these particularly preferred pharmaceutical compositions in liquid form the low viscosity grade sodium alginate employed preferably has a viscosity, when determined in the above-described manner, in the range of from 3 to 40 centipoise, most preferably in the range of from 3 to 20 centipoise.

Examples of the various types of suspending agents that may be employed for the sodium salt of an acrylic polymer cross-linked by less than 3% allyl-sucrose are the sodium salts of the Carbopols 934, 940 and 941 (B. F. Goodrich Chemical Company) and preferably of Carbopol 934. Examples of the other types are for pectin — apple pectin, for pregelatinised potato starch — Prejel 97 (H. Helias & Co., London) and for sodium starch glycolate — Primojel (Verenigde Zetmeelbdrijven, Holland).

The liquid compositions of the present invention are aqueous compositions and they are therefore susceptible to contamination and subsequent deterioration by microorganisms. Consequently the liquid compositions will preferably contain a preservative. A combination of methyl and propyl p-hydroxybenzoates may be employed, for example in an amount of 0.4% and 0.06% weight/volume, respectively.

The pharmaceutical compositions of the present invention may also include one or more of a colouring, sweetening or flavouring agent.

The pharmaceutical compositions of the present invention in liquid form are palatable and relatively easy to swallow since there is no alginic acid present in these compositions to react with the sodium bicarbonate and lead to foaming in the buccal cavity. When the compositions contact the gastric acid a relatively rigid gelatinous precipitate of alginic acid is formed. The sodium bicarbonate and calcium carbonate present in the composition react with the gastric acid to form carbon dioxide which is entrapped in the gel. The carbonated gel has a lower bulk density than the gastric acid and floats to the surface. The calcium ions serve to cross-link the precipitated alginic acid molecules and thereby strengthen the gel matrix.

It will be understood that the rigidity, strength and thickness of the raft formed in contact with gastric acid will depend upon the ratio of sodium bicarbonate and calcium carbonate to sodium alginate, and upon the viscosity of the sodium alginate.

The invention is illustrated by the following non-limiting Examples:

EXAMPLE 1

A liquid preparation having the following formulation:

| | |
|---|---|
| sodium alginate (Protanal LF 5/60) | 5.00 g |
| sodium bicarbonate | 2.67 g |
| calcium carbonate B.P. (Sturcal L) (median particle size 8.0 microns, density 0.78 to 0.89 grams per ml) | 1.60 g |
| Carbopol 934 | 0.65 g |
| methyl p-hydroxybenzoate | 0.40 g |
| propyl p-hydroxybenzoate | 0.06 g |
| sodium hydroxide | 0.30 g approx. |
| sweetening agent, colour, flavouring | 0.17 g |
| water | to 100.00 ml | was prepared as follows. The sodium bicarbonate, methyl p-hydroxybenzoate, and propyl p-hydroxybenzoate were dissolved, with agitation, in about 50 mls of water. Sodium alginate was added with vigorous stirring to ensure rapid dispersion. When the sodium alginate had dissolved the calcium carbonate was added with continued stirring. The Carbopol was dispersed, with agitation, in about 40 mls of water in a separate vessel. Aqueous sodium hydroxide was added to the Carbopol mixture to raise the pH to 7, after which the sodium alginate mixture was added and thoroughly blended. Following the addition of sweetening, colour and flavouring agents additional water was added to a volume of 100 ml.

The resultant product had a creamy consistency and was readily pourable into a dose measuring vessel and was physically and chemically stable over a period of six months at ambient temperature.

EXAMPLE 2

The formulation of the liquid preparation of Example 1 was varied by replacing the grade of sodium alginate used therein by 2.50 grams Protanal LF 250.

EXAMPLES 3 TO 10

The formulation of the liquid preparation of Example 1 was varied by employing differing quantities of the sodium alginate (Protanal LF 5/60) sodium bicarbonate and calcium carbonate.

| Example No | 3 | 4 | 5 | 6 | 7 | 8 | 9 | 10 |
|---|---|---|---|---|---|---|---|---|
| sodium alginate | 2.5 | 2.5 | 2.5 | 2.5 | 8.0 | 8.0 | 8.0 | 8.0g |
| sodium bicarbonate | 1.3 | 4.3 | 4.3 | 1.3 | 4.3 | 4.3 | 1.3 | 1.3g |
| calcium carbonate | 0.8 | 2.6 | 0.8 | 2.6 | 2.6 | 0.8 | 2.6 | 0.8g |

EXAMPLE 11

The formulation of the liquid preparation of Example 1 was varied by replacing the Carbopol 934 by 0.75 g of Carbopol 941.

EXAMPLES 12 TO 15

The formulation of the liquid preparation of Example 1 was varied by replacing the Carbopol 934 and the sodium hydroxide by other suspending agents:

| | |
|---|---|
| Example 12 | Tragacanth 1.0% |
| Example 13 | Apple pectin 1.5% |
| Example 14 | Pregelatinised potato starch (Prejel 97) 1% |

-continued

| Example 15 | Sodium starch glycolate (Primojel) 1% |

The following comparative Examples A, B and C are of liquid formulations which do not fall within the scope of the present invention.

EXAMPLE A

The formulation of the liquid preparation of Example 1 was varied by replacing the grade of sodium alginate by 2.5 g of Protanal HF 120 of a higher viscosity (a 1% aqueous solution as determined on a Brookfield viscometer, model RVT, employing a No 1 spindle at 20 r.p.m. and a temperature of 25° C. had viscosity of 330 cps).

EXAMPLE B

The formulation of the liquid preparation of Example 1 was varied by omitting the calcium carbonate therefrom.

EXAMPLE 16

The formulation of the liquid preparation of Example 1 was varied by replacing the grade of sodium alginate used therein by 5.0 g of Protanal LF 5/120 M.

EXAMPLE 17

The formulation of the liquid preparation of Example 1 was varied by replacing the grade of sodium alginate used therein by 4.0 g of Manucol LHF and by omitting the Carbopol 934.

EXAMPLE 18

The formulation of the liquid preparation of Example 1 was varied by replacing the grade of sodium alginate used therein by 8.0 g of Manucol LHF, by omitting the Carbopol 934, and by using water at 80° C. in the mixing process.

EXAMPLE 19

The formulation of the liquid preparation of Example 1 was varied by replacing the grade of sodium alginate used therein by 5.0 g of Protanal LF 250 and by omitting the Carbopol 934.

EXAMPLE 20

The formulation of the liquid preparation of Example 1 was varied by replacing the grade of sodium alginate used therein by 8.0 g of Protanal LF 250, by omitting the Carbopol 934, and by using water at 80° C. in the mixing process.

EXAMPLE 21

The formulation of the liquid preparation of Example 1 was varied by replacing the grade of sodium alginate used therein by 5.0 g of Manucol LB.

EXAMPLE C

The formulation of the liquid preparation of Example 1 was varied by replacing the grade of sodium alginate used therein by 2.5 g of Protanal SF 250 of a higher viscosity (a 1% aqueous solution as determined on a Brookfield viscometer model RVT employing a No 1 spindle at 20 r.p.m. had a viscosity of 225 cps).

The ability of the compositions to form a raft or mechanical barrier floating on the stomach contents and thereby to suppress gastric reflux was assessed by their ability to form a raft in an in vitro test. In the test a 20 ml aliquot of a liquid preparation was added to a beaker containing 150 mls of 0.1 N hydrochloric acid. The time taken for the precipitate of alginic acid to rise to the surface of the hydrochloric acid was measured. The thickness of the raft 30 seconds and 2 minutes after the addition was also measured. A subjective assessment of the rigidity of the raft was also made.

The following are the results obtained with the Examples and Comparative Examples A, B and C when evaluated by the above-described testing method.

The raft obtained in Example 1 was deemed in the subjective assessment of raft rigidity to be rigid and stable. The rigidity of the rafts formed by the liquid preparations of the other Examples and the Comparative Examples are described below in relation to the rigidity of the raft of Example 1.

| Example No | Rise time (sec) | Raft Thickness (mm) 30 sec | 2 min | Comments |
|---|---|---|---|---|
| 1 | 15 | 20 | 25 | Rigid, stable raft. |
| 2 | 8 | 12 | — | Softer raft than Example 1 containing less carbon dioxide. |
| 3 | 30 | 28 | 23 | Rigid, stable raft as in Example 1. |
| 4 | 20 | 43 | 42 | Slightly less rigid raft than Example 1. |
| 5 | 15 | 42 | 38 | Softer raft than Example 1. |
| 6 | 15 | 32 | 29 | Less rigid raft than Example 1. |
| 7 | 24 | 32 | 37 | Rigid, stable raft as in Example 1. |
| 8 | 18 | 31 | 40 | More carbon dioxide in upper layers of raft. Less rigid than Example 1. |
| 9 | 30 | 20 | 16 | Raft as rigid as Example 1 but with an uneven lower surface. |
| 10 | 30 | 21 | 16 | More rigid raft than Example 1. |
| 11 | 14 | 15 | 25 | Raft as rigid as Example 1. |
| 12 | 12 | 48 | — | More rigid raft than Example 1. |
| 13 | 6 | 47 | — | More rigid raft than Example 1. |
| 14 | 22 | 54 | — | As rigid as Example 1. |
| 15 | 25 | 41 | — | As rigid as Example 1. |
| A | — | — | — | Product too viscous to manufacture. |
| B | 9 | 15 | 25 | Raft not as rigid or cohesive as Example 1. Lower layer of raft tends to sink in the acid |
| 16 | 10 | 15 | 15 | More compact less rigid raft than Example 1 |
| 17 | 6 | 17 | 18 | More compact less rigid raft than Example 1 |
| 18 | 7 | 12 | 12 | More compact more rigid raft than Example 1 |
| 19 | 10 | 10 | 10 | More compact less rigid raft than Example 1 |
| 20 | 5 | 14 | 14 | More compact more rigid raft than Example 1 |
| 21 | 5 | 25 | — | Rigid, stable, raft |
| C | — | — | — | Product too viscous to manufacture |

EXAMPLE 22

A dry powder was prepared by thoroughly mixing and blending the following ingredients:

| | |
|---|---|
| sodium alginate (Protanal LF 5/60) | 1.00 g |
| sodium bicarbonate | 0.534 g |
| calcium carbonate B.P. (Sturcal L) (median particle size 8.0 microns, density 0.78 to 0.89 grams per ml) | 0.320 g |

Conveniently the powder may be packaged in a sachet; for the purposes of administration the powder is added to about 20 mls of water, thoroughly mixed therewith and the liquid preparation drunk by the patient. For the purposes of evaluation by the above-described testing method the powder (1.854 g) was added to 20 ml of water and thoroughly mixed therewith. The resultant liquid preparation gave the following results:

| Example No | Rise time (sec) | Raft Thickness (mm) 30 sec | 2 min | Comments |
|---|---|---|---|---|
| 21 | 2 | 40 | 36 | Rigid, stable raft. |

For the suppression of gastric reflux the normal oral dose for an adult of a composition of the invention will be one containing 0.4 g to 1.5 g of sodium alginate. For the purposes of convenience and accuracy of dosing the compositions may advantageously be employed in a unit dosage form in, for example, a sachet containing from 0.4 g to 1.5 g of sodium alginate.

I claim:

1. A pharmaceutical composition for the suppression of gastric reflux comprising a low viscosity grade sodium alginate for which the viscosity of a 1% aqueous solution, when determined on a Brookfield viscometer model RVT using spindle No 1 at 20 r.p.m. at 25° C., is within the range of from 3 to 60 centipoise, from 0.16 to 2.60 parts by weight of sodium bicarbonate per part by weight of sodium alginate and from 0.10 to 1.04 parts by weight of calcium carbonate per part by weight of sodium alginate.

2. A pharmaceutical composition according to claim 1 wherein the sodium bicarbonate is present in an amount of from 0.33 to 0.88 parts by weight per part by weight of sodium alginate and the calcium carbonate is present in an amount of from 0.2 to 0.5 parts by weight per part by weight of sodium alginate.

3. A pharmaceutical composition according to claim 1 which is in the form of a dry powder.

4. A pharmaceutical composition in liquid form for the suppression of gastric reflux comprising an aqueous medium containing 2.5 to 8.0% weight/volume of a low viscosity grade sodium alginate for which the viscosity of a 1% aqueous solution, when determined on a Brookfield viscometer model RVT using spindle No 1 at 20 r.p.m. at 25° C., is within the range of from 3 to 60 centipoise, 1.3 to 6.5% weight/volume of sodium bicarbonate and 0.8 to 2.6% weight/volume of calcium carbonate.

5. A pharmaceutical composition according to claim 4 which further includes a suspending agent in an amount effective to maintain the calcium carbonate in suspension.

6. A pharmaceutical composition according to claim 5 wherein the suspending agent is present in an amount of from 0.3 to 1.7% weight/volume and is selected from the group consisting of the sodium salt of an acrylic polymer cross-linked with less than 3% allyl-sucrose, tragacanth, pectin, pregelatinised potato starch, sodium starch glycolate and mixtures thereof.

7. A pharmaceutical composition according to claim 4 comprising an aqueous medium containing 4.0 to 6.0% weight/volume of a low viscosity grade sodium alginate for which the viscosity of a 1% aqueous solution, when determined on a Brookfield viscometer model RVT using spindle No 1 at 20 r.p.m. at 25° C., is within the range of from 3 to 60 centipoise, 2.0 to 3.5% weight/volume of sodium bicarbonate, 1.2 to 2.0% weight/volume of calcium carbonate and 0.6 to 1.2% weight/volume of the sodium salt of an acrylic polymer cross-linked with 1% allyl-sucrose.

8. A pharmaceutical composition according to claim 7 wherein the low viscosity grade sodium alginate has a viscosity in the range of from 3 to 40 centipoise.

9. A pharmaceutical composition according to claim 7 wherein the low viscosity grade sodium alginate has a viscosity in the range of from 3 to 20 centipoise.

10. A pharmaceutical composition according to claim 4 which further includes a preservative.

11. A pharmaceutical composition according to claim 10 wherein the preservative is a mixture of methyl p-hydroxybenzoate and propyl p-hydroxybenzoate which are employed in an amount of 0.4% weight/volume and 0.06% weight/volume, respectively.

12. A pharmaceutical composition in dry powder form adapted to be mixed with water and drunk by a person in need of suppressing gastric reflux consisting essentially of a low viscosity grade sodium alginate for which the viscosity of a 1% aqueous solution, when determined on a Brookfield viscometer model RVT using spindle No 1 at 20 r.p.m. at 25° C., is within the range of from 3 to 60 centipoise, from 0.16 to 2.60 parts by weight of sodium bicarbonate per part by weight of sodium alginate and from 0.10 to 1.04 parts by weight of calcium carbonate per part by weight of sodium alginate.

13. A pharmaceutical composition in liquid form for the suppression of gastric reflux consisting essentially of the following ingredients in an aqueous medium: from 2.5 to 8.0% weight/volume of a low viscosity grade sodium alginate for which the viscosity of a 1% aqueous solution, when determined on a Brookfield viscometer model RVT using spindle No 1 at 20 r.p.m. at 25° C., is within the range of from 3 to 40 centipoise, 1.3 to 6.5% weight/volume of sodium bicarbonate and 0.8 to 2.6% weight/volume of calcium carbonate.

14. A method of treating humans for gastric reflux comprising orally administering to a human an amount of a liquid composition, as defined below, effective to provide relief, said liquid composition comprising an aqueous medium containing 2.5 to 8.0 weight/volume of a low viscosity grade sodium alginate for which the viscosity of a 1% aqueous solution, when determined on a Brookfield viscometer model RVT using spindle No. 1 at 20 r.p.m. at 25° C. is within the range of from 3 to 60 centipoise, 1.3 to 6.5 weight/volume of sodium bicarbonate and 0.8 to 2.6 weight/volume of calcium carbonate, said ingredients reacting in the presence of gastric acid in the stomach to form a carbonated gel in which alginic acid molecules are cross-linked by calcium ions to strength the gel matrix.

* * * * *